(12) United States Patent
Ichikawa et al.

(10) Patent No.: US 8,955,971 B2
(45) Date of Patent: Feb. 17, 2015

(54) FUNDUS PHOTOGRAPHING APPARATUS

(75) Inventors: Naoki Ichikawa, Okazaki (JP); Yoshiaki Mimura, Gamagori (JP)

(73) Assignee: Nidek Co., Ltd., Gamagori-Shi (JP)

( * ) Notice: Subject to any disclaimer, the term of this patent is extended or adjusted under 35 U.S.C. 154(b) by 41 days.

(21) Appl. No.: 13/407,022

(22) Filed: Feb. 28, 2012

(65) Prior Publication Data

US 2012/0224141 A1 Sep. 6, 2012

(30) Foreign Application Priority Data

Mar. 1, 2011 (JP) .................................. 2011-043529

(51) Int. Cl.
  *A61B 3/14* (2006.01)
  *A61B 3/00* (2006.01)
  *A61B 3/10* (2006.01)
  *A61B 3/12* (2006.01)

(52) U.S. Cl.
  CPC .... *A61B 3/12* (2013.01); *A61B 3/14* (2013.01)
  USPC ........... 351/206; 351/200; 351/205; 351/210; 351/221

(58) Field of Classification Search
  CPC ............ A61B 3/14; A61B 3/12; A61B 3/145; A61B 3/113; A61B 3/1208; A61B 3/1015
  USPC .................. 351/200, 205–206, 210, 221, 246
  See application file for complete search history.

(56) References Cited

U.S. PATENT DOCUMENTS

| | | | |
|---|---|---|---|
| 2004/0142485 A1 | 7/2004 | Flower et al. | |
| 2006/0139572 A1* | 6/2006 | Noda et al. ..................... | 351/206 |
| 2009/0323022 A1 | 12/2009 | Uchida | |
| 2010/0165292 A1* | 7/2010 | Mizuochi ...................... | 351/206 |
| 2011/0001929 A1* | 1/2011 | Tawada ......................... | 351/208 |
| 2013/0188142 A1 | 7/2013 | Uchida | |

FOREIGN PATENT DOCUMENTS

JP    A-2007-202724    8/2007

* cited by examiner

*Primary Examiner* — Dawayne A Pinkney
(74) *Attorney, Agent, or Firm* — Oliff PLC (57) ABSTRACT

A fundus photographing apparatus comprises: an anterior-segment observation optical system arranged to image an anterior-segment illuminated with infrared light to obtain an anterior-segment image; a fundus photographing optical system arranged to image a fundus illuminated with visible light emitted from a light source to obtain a fundus image; a display controller arranged to selectively display the fundus image and the anterior-segment image on a monitor; a photographing switch for inputting a photographing start signal to start photographing using the fundus photographing optical system; and a time informing part arranged to inform an elapsed time after the photographing start signal is input with the photographing switch or an elapsed time after the visible light is emitted from the light source, wherein the display controller displays the elapsed time informed by the time informing part together with the anterior-segment image on the monitor.

6 Claims, 5 Drawing Sheets

FUNDUS PHOTOGRAPHING APPARATUS

CROSS-REFERENCE TO RELATED APPLICATIONS

This application is based upon and claims the benefit of priority from the prior Japanese Patent Application No. 2011-043529, filed on Mar. 1, 2011, the entire contents of which are incorporated herein by reference.

TECHNICAL FIELD

The present invention relates to a fundus photographing apparatus for photographing a fundus of an examinee's eye.

BACKGROUND ART

As fundus photographing apparatuses, there are known a mydriatic type apparatus and a non-mydriatic type apparatus. The mydriatic type apparatus is configured to photograph a fundus of an eye with a pupil dilated by instillation of mydriatic drops. The non-mydriatic type apparatus is configured to photograph a fundus by using infrared light as observation illumination light without instilling mydriatic drops in an eye (JP 2007-202724 A).

DISCLOSURE OF THE INVENTION

Problems to be Solved by the Invention

Since the non-mydriatic fundus photographing apparatus is used for photographing without mydriatic drops, the eye constricts by illumination of visible light during photographing. For example, when one examinee is to be photographed several times, i.e., when his/her both eyes are to be photographed, it is necessary to wait for each pupil constricted once to dilate naturally to a photographable degree. However, a time required for natural mydriasis or dilatation is different from examinee to examinee. It is therefore difficult to easily ascertain how long it will be necessary to wait until photographing is enabled again.

The present invention has been made in view of the circumstances and has a purpose to provide a fundus photographing apparatus capable of determining appropriate timing to photograph an examinee's eye.

Means of Solving the Problems

To achieve the above purpose, one aspect of the invention provides a fundus photographing apparatus comprising: an anterior-segment observation optical system arranged to image an anterior-segment illuminated with infrared light to obtain an anterior-segment image; a fundus photographing optical system arranged to image a fundus illuminated with visible light emitted from a light source to obtain a fundus image; a display controller arranged to selectively display the fundus image and the anterior-segment image on a monitor; a photographing switch for inputting a photographing start signal to start photographing using the fundus photographing optical system; and a time informing part arranged to inform an elapsed time after the photographing start signal is input with the photographing switch or an elapsed time after the visible light is emitted from the light source, wherein the display controller displays the elapsed time informed by the time informing part together with the anterior-segment image on the monitor.

MODE FOR CARRYING OUT THE INVENTION

Figure 1:
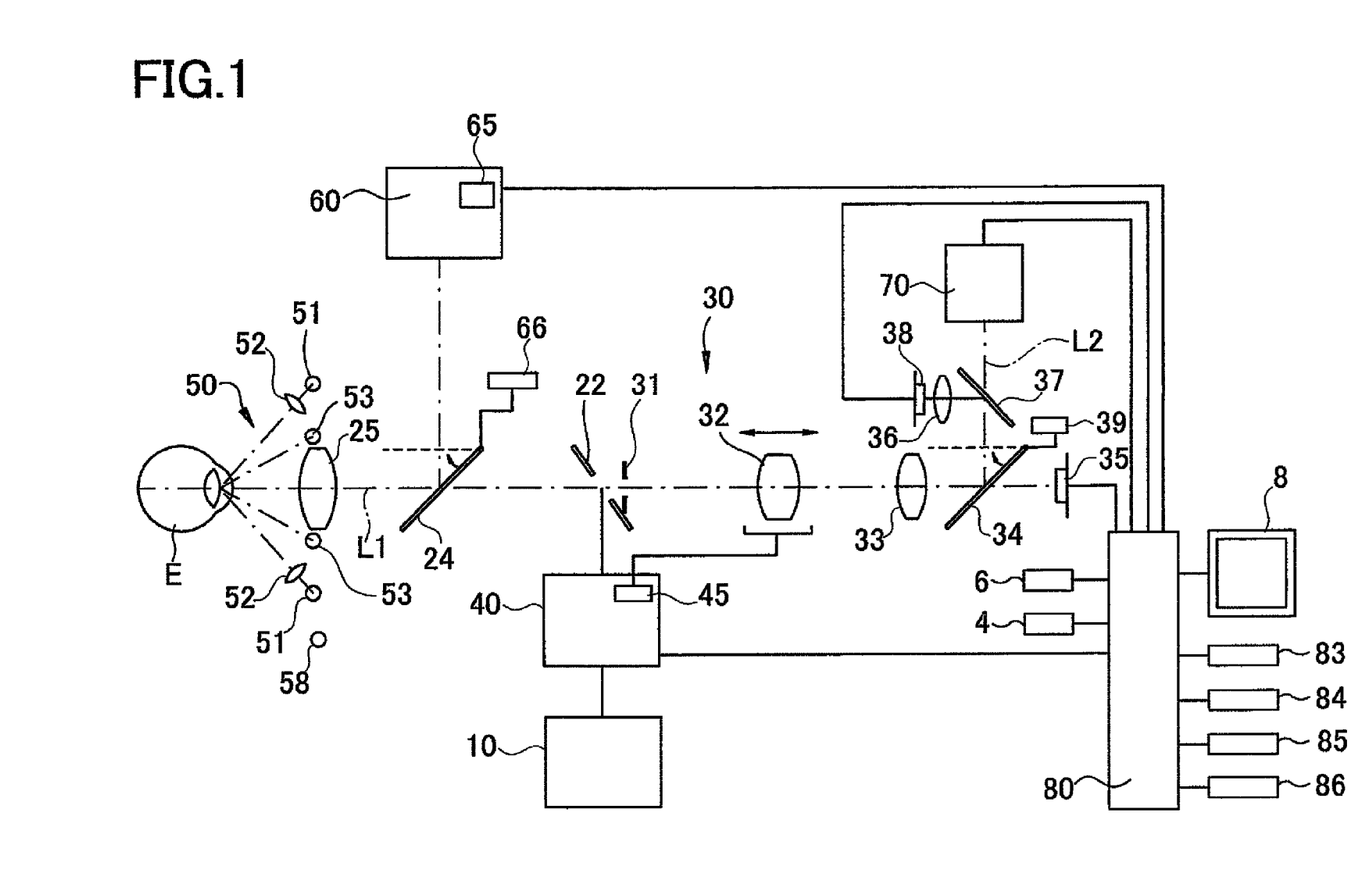
FIG. 1 is a schematic configuration view of an optical system and a control system.

A detailed description of a preferred embodiment of the present invention will now be given referring to the accompanying drawings. FIG. 1 is a schematic configuration view of an optical system and a control system of a fundus photographing apparatus (a fundus camera). The optical system includes an illumination optical system 10, fundus observation and photographing optical system 30 for observing and photographing a fundus, a split-index projecting optical system 40 for projecting a split index (a focus index) onto a fundus, an alignment-index projecting optical system 50 for projecting an alignment index light onto an anterior segment, an anterior-segment observation optical system 60 for photographing an anterior segment, and a fixation target presenting optical system 70 for inducing a visual line of an eye.

<Illumination Optical System>

The illumination optical system 10 includes an observation illumination optical system and a photographing illumination optical system. The observation illumination optical system illuminates a fundus with infrared light emitted from an infrared light source (not shown) that emits a near-infrared light beam. The photographing illumination optical system illuminates a fundus with visible light emitted from a photographing visible light source (not shown) such as a flash lamp and LED. The light beam from the above illumination optical system 10 illuminates the fundus through a perforated monitor 22, a dichroic mirror (a wavelength selecting mirror) 24, and an objective lens 25.

The dichroic mirror 24 has the wavelength property of transmitting wavelengths from the infrared light source of the observation illumination optical system but reflecting infrared light from the alignment index projecting optical system 50 mentioned later. The dichroic mirror 24 is placed in a slanted state to be removably insertable in an optical path by an inserting/removing mechanism 66 consisting of a solenoid, a cam, and others. Specifically, this mirror 24 is disposed in the slanted state in the optical path during observation of a fundus through the observation illumination optical system but is removed from the optical path during photographing of the fundus through the photographing illumination optical system.

<Fundus Observation and Photographing Optical System>

The fundus observation and photographing optical system 30 includes the fundus observation optical system and the fundus photographing optical system. The fundus observation optical system includes the objective lens 25, a photographing diaphragm 31, a focusing lens 32, an image forming lens 33, and a flip-up mirror 34.

The photographing diaphragm 31 is placed in a position near an aperture of the perforated mirror 22 and approximately conjugate with a pupil of an eye E with respect to the objective lens 25. The focusing lens 32 is moved along an optical axis direction by a moving mechanism 45 provided with a motor. The flip-up mirror 34 is inserted in or removed from the optical path by an inserting/removing mechanism 39.

In an optical path extending in a reflecting direction of the flip-up mirror 34, there are placed a dichroic mirror 37, a relay lens 36, and a imaging element 38. The dichroic mirror 37 has the property of reflecting infrared light but transmitting visible light. The imaging element 38 is sensitive to an infrared wavelength region and images an image of the fundus illuminated with infrared light.

The fundus photographing optical system shares the objective lens 25 and the optical components from the photographing diaphragm 31 to the image forming lens 33 with the fundus observation optical system. The fundus photographing optical system further includes an imaging element 35 sensitive to a visible wavelength region and images the image of the fundus illuminated with visible light.

During observation of the fundus, the light beam emitted from the infrared light source passes through the dichroic mirror 24 and converges once near the pupil of the eye E through the objective lens 25, and then diffuses to illuminate the fundus of the eye E. Reflection light from the fundus passes through the objective lens 25, the dichroic mirror 24, the aperture of the perforated mirror 22, the photographing diaphragm 31, the focusing lens 32, the image forming lens 33, the flip-up mirror 34, the dichroic mirror 37, and the relay lens 36, and forms an image on the imaging element 38.

During photographing of the fundus, while the dichroic mirror 24 and the flip-up mirror 34 are removed from the optical path by driving of the inserting/removing mechanisms 66 and 39, reflection light from the fundus illuminated with the visible light source passes through the objective lens 25, the aperture of the perforated mirror 22, the photographing diaphragm 31, the focusing lens 32, and the image forming lens 33, and forms an image on the imaging element 35.

<Split Index Projecting Optical System>

The split index projecting optical system 40 includes an infrared light source (not shown) that emits a near-infrared light beam. The light beam from the infrared light source passes through a well-known split index plate and a spot mirror and then reflected, passing through the perforated mirror 22, the dichroic mirror 24, and the objective lens 25, and is projected on the fundus of the eye E. The light beam from the split index projecting optical system 40 is projected in a split state on the eye E when the beam is out of focus, whereas in a coincident state when the beam is in focus on the fundus. Split index images projected on the fundus are captured together with a fundus image by the imaging element 38 for fundus observation.

<Alignment Index Projecting Optical System>

The alignment index projecting optical system 50 includes a plurality of infrared light sources arranged concentrically about a photographing optical axis L1. To be specific, there are provided a first index projecting optical system including right and left sets of infrared light sources 51 and collimating lenses 52, the sets being placed symmetric with respect to a vertical plane passing through the photographing optical axis L1 (0° and 180°), and a second index projecting optical system including a plurality of infrared light sources 53 arranged in positions different from the first index projecting optical system. The first index projecting optical system projects targets at infinity onto a cornea of the eye E obliquely from right and left sides thereof. The second index projecting optical system projects targets at finity onto the cornea of the eye E obliquely from upper and lower sides or oblique sides.

<Anterior-segment Observation Optical System>

Figure 2A:
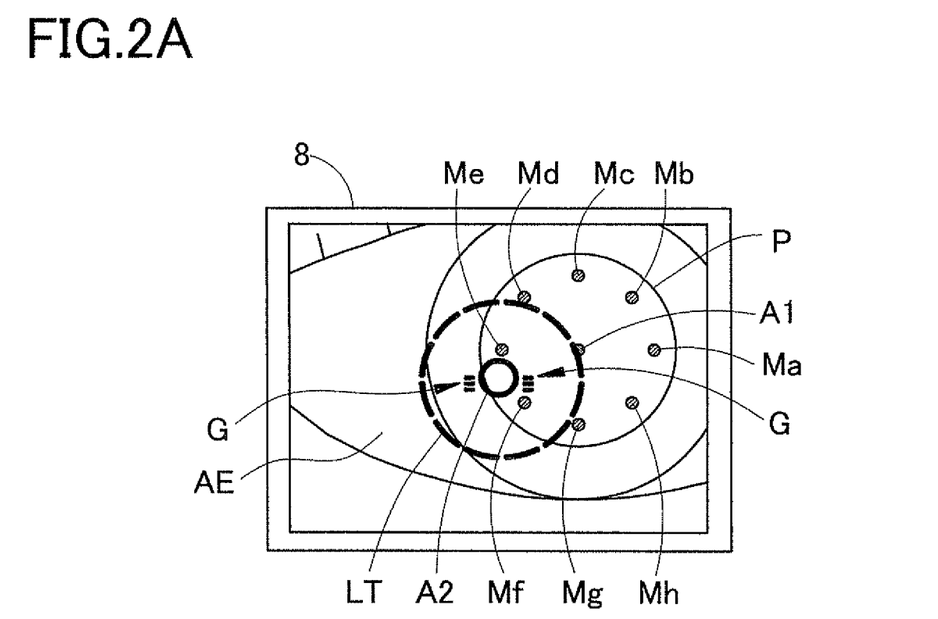
FIG. 2A shows an example of an anterior-segment image displayed on a monitor.
Figure 2B:
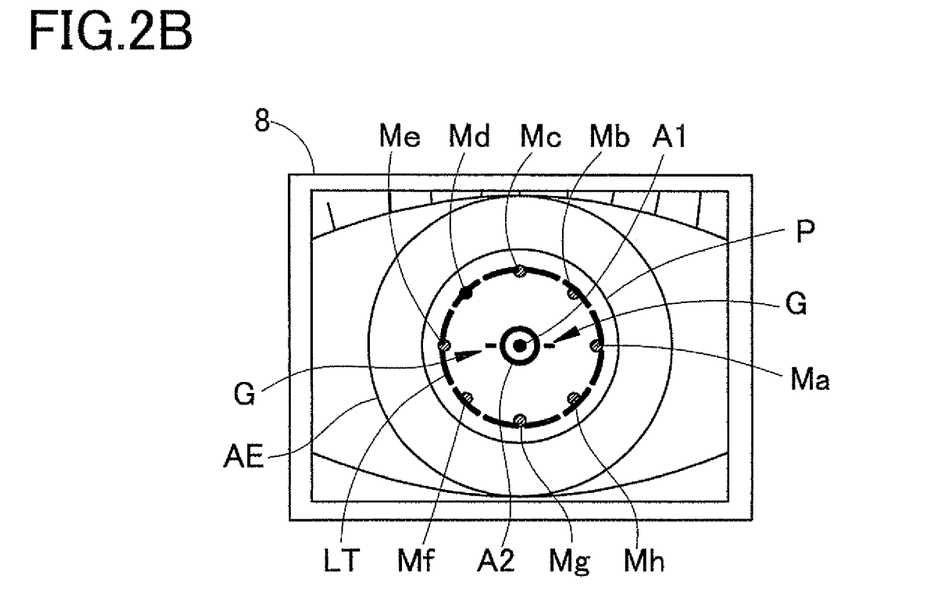
FIG. 2B shows an example of the anterior-segment image displayed on the monitor.

The anterior-segment observation optical system 60 is placed in a reflecting direction of the dichroic mirror 24 and includes an imaging element 65 for imaging an anterior segment illuminated by the anterior-segment illumination light source 58 and alignment indexes. Furthermore, when the light sources of the alignment index projecting optical system 50 are turned on, the imaging element 65 detects corneal reflection light of the alignment light. When a controller 80 receives an output of the imaging element 65, an anterior-segment image AE is displayed on a monitor 8 (see FIG. 2). It is to be noted that an alignment state of an apparatus main unit with respect to the eye is detected by the anterior-segment observation optical system 60 and further a pupil shape of the eye is obtained from the anterior-segment image captured by the imaging element 65.

<Fixation Target Presenting Optical System>

The fixation target presenting optical system 70 includes a visible light source (not shown) and a target presenting section (not shown). By presenting a fixation target at different positions with respect to an optical axis L2, photographing is switched between standard photographing to photograph a central portion of the fundus and peripheral, photographing to photograph a peripheral portion of the fundus. As the target presenting section, well-known structures are selected, such as a liquid crystal display, a combination of a light-shielding plate formed with a plurality of openings and a drive mechanism, and others.

<Control System>

The controller 80 controls various operations of the fundus photographing apparatus. To the controller 80, there are connected the above imaging elements 5, 38, and 65, the inserting/removing mechanism 39, the moving mechanism 45, the inserting/removing mechanism 66, each light source, and others. In addition, to the controller 80, there are connected a joystick 4 for moving the apparatus main unit, back and forth, and right and left, with respect to the eye, a drive unit 6 for moving a photographing part including the above optical systems and the control system in three-dimensional directions with respect to the eye, the monitor 8 for displaying an anterior-segment image and a fundus observation (photographing) image, a photographing switch 83 for inputting a trigger signal to start photographing, an input switch 84 for inputting information such as examinee's age, a memory 85, a timer (a time measuring device) 86 for counting an elapsed time of photographing, and others.

The controller 80 determines an alignment deviation amount of the photographing part with respect to the eye based on a photographing signal from the imaging element 65 and performs alignment between the eye and the photographing part, and further determines a pupil shape and a center position (pupil center). Furthermore, a reticule LT representing the size of a pupil diameter required for photographing is electronically displayed on a screen (see FIG. 2) of the monitor 8 on which the anterior-segment image AE appears. In addition, an alignment index A1 whose display position is changed according to the alignment deviation amount and a mark A2 to be used for alignment of the alignment index A1 are electronically displayed on the monitor 8.

In the present embodiment, the controller 80 controls to change a display state of the reticule LT in synchronization with the operation of the timer 86. That is, the reticule LT represents a waiting time required from a previous photographing time to a next photographing time (waiting time information) and also an elapsed time from the previous photographing time (elapsed time information) based on the changing display state of the reticule LT. The details of the elapsed-time indication using the reticule LT will be mentioned later.

The controller 80 causes the monitor 8 to display the fundus image imaged by the imaging element 38 and also performs focus alignment with the fundus based on an optical split state of split index images detected by the imaging element 38.

Operations of the fundus photographing apparatus configured as above will be explained below. The following explanation is given to an example of standard photographing to photograph with a focus on the vicinity of a posterior fundus of each of right and left eyes of an examinee. An examiner first inputs various information such as examinee's age by operation of the input switch 84. While the examinee gazes at a lighted light source of the fixation target presenting optical system 70, the examiner operates the joystick 4 to move the photographing part not shown toward the eye E (herein, a right eye) so that the anterior-segment image AE and the alignment index image appear on the monitor 8.

FIG. 2 show an example of the anterior-segment image AE displayed on the monitor 8; FIG. 2A shows an out-of-alignment state and FIG. 2B shows an in-alignment state. When the alignment index image projected on the cornea of the eye is detected by the imaging element 65, the controller 80 determines, as an approximate cornea vertex (an alignment reference point), X-Y coordinates of the center of a ring pattern consisting of index images Ma to Mh projected circularly, and electronically displays the alignment index A1. The controller 80 further electronically displays the mark A2 serving as a target of alignment on the monitor 8 in a position corresponding to a reference in the X and Y directions previously set on the imaging element 65. For instance, the reference position in the X and Y directions is determined as an intersecting point between a photographing plane of the imaging element 65 and the photographing optical axis L1. The controller 80 causes the monitor 8 to display the reticule LT representing a desired pupil diameter around a display position of the mark A2.

The examiner moves the photographing part by operating the joystick 4 to adjust the mark A2 to the alignment index A1. The controller 80 determines a deviation amount in the X and Y directions from the positions of the alignment index A1 and the mark A2. By comparing an interval between infinite index images Ma and Me and an interval between finite index images Mh and Mf, an alignment deviation amount in a Z direction is determined. Further, it is determined whether or not the alignment deviation amounts in three-dimensional directions satisfy an alignment permissible range so that the mark A2 agrees with the alignment index A1. The alignment in a working distance direction is represented by an increase or decrease in the number of indicators G displayed on the monitor 8. Thus, the examiner adjusts the working distance by operating the joystick 4 until the number of indicators G becomes one.

In the above way, it is checked whether or not a pupil diameter P of the eye has such a size that does not partially overlap the reticule LT in proper alignment state as shown in FIG. 2B. It is to be noted that the reticule LT in the present embodiment has a function of indicating the waiting time information and the elapsed time information as mentioned above. In the first photographing, however, the controller 80 sets that measurement of an elapsed time from previous photographing by the timer 86 is not performed. In this case, the reticule LT is displayed in a constant state.

Figure 3:
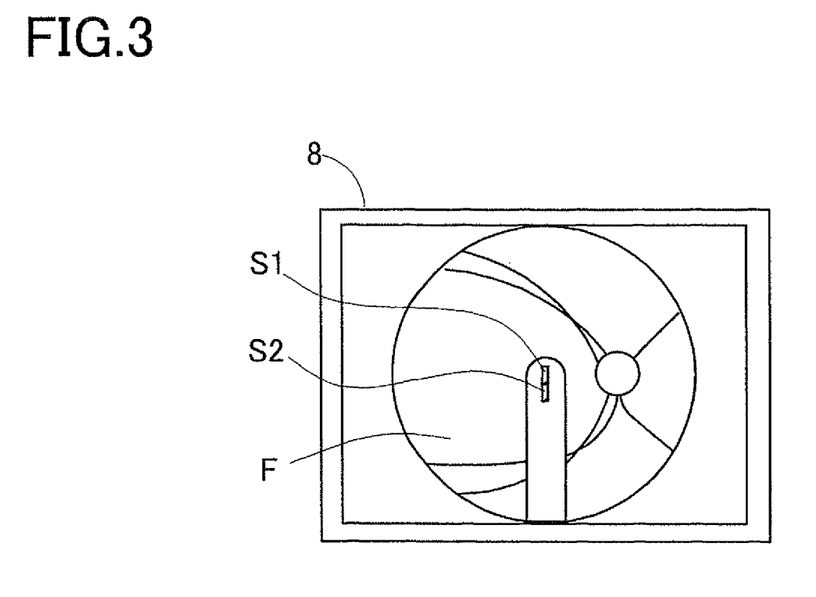
FIG. 3 shows an example of a fundus image displayed on the monitor.

Upon completion of alignment, the controller 80 performs focusing on the fundus. Specifically, based on an input signal by a predetermined operation of the examiner, the controller 80 switches a display on the monitor 8 from the anterior-segment image AE to a fundus image F imaged by the imaging element 38. FIG. 3 shows an example of the fundus image displayed on the monitor 8. When split index images S1 and S2 projected on the vicinity of the posterior pole of the fundus are captured by the imaging element 38, the controller 80 detects their split, or separate, state and drives the moving mechanism 45 to move the focusing lens 32 along the optical axis so that the split indexes S1 and S2 are aligned with each other to adjust a focus on the fundus.

While the focus is proper as shown in FIG. 3, when the photographing switch 83 is pressed, the controller 80 starts the measurement of the elapsed time of photographing by the timer 86 in response to a trigger signal from the switch 83. The controller 80 also starts a fundus photographing operation. Specifically, the controller 80 drives the inserting/removing mechanisms 66 and 39 to move the dichroic mirror 24 and the flip-up mirror 34 respectively out of the photographing optical axis L1 and turns on the visible light source of the fundus photographing optical system. Reflection light from the fundus E illuminated with visible light passes through the objective lens 25 and the optical components from the photographing diaphragm 31 to the image forming lens 33, and then is received by the imaging element 35. An image imaged by the imaging element 35 is stored in the memory 85.

In this embodiment, the measurement of an elapsed time of photographing is started in response to the trigger signal from the photographing switch 83. As an alternative, the measurement of an elapsed time of photographing may be started in response to turn-on of the visible light source as a trigger signal.

To photograph the other eye (herein, a left eye) of the same examinee, the examiner performs positioning between the photographing part and the eye (left eye) by the same operation as above so that an anterior-segment image AE is displayed again on the monitor 8.

Meanwhile, with the non-mydriatic fundus photographing apparatus as disclosed in the present embodiment, photographing is carried out without instillation of mydriatic drops in the eye. Thus, the pupil constricts in reaction to the visible light projected on the fundus during photographing. When one examinee is to be photographed several times, accordingly, it is necessary to wait for each pupil to naturally dilate to a photographable size. It is however difficult to judge a natural mydriatic state, and hence such judgment likely depends on differences in skill level or the like between examiners. If photographing is erroneously performed even though the pupil is in an insufficient mydriatic state, re-photographing is needed, resulting in an increased load on a patient.

In the present embodiment, therefore, while the anterior-segment image is being displayed on the monitor 8, the information of a waiting time required from previous photographing to next photographing and the information of an elapsed time obtained by the timer 86 serving as a time informing part are displayed on the same screen of the monitor 8. In association with the elapsed time from the photographing time measured by the timer 86, a display state of the reticule LT is changed. This makes it easy for the examiner to ascertain the elapsed time from previous photographing.

Figure 4:
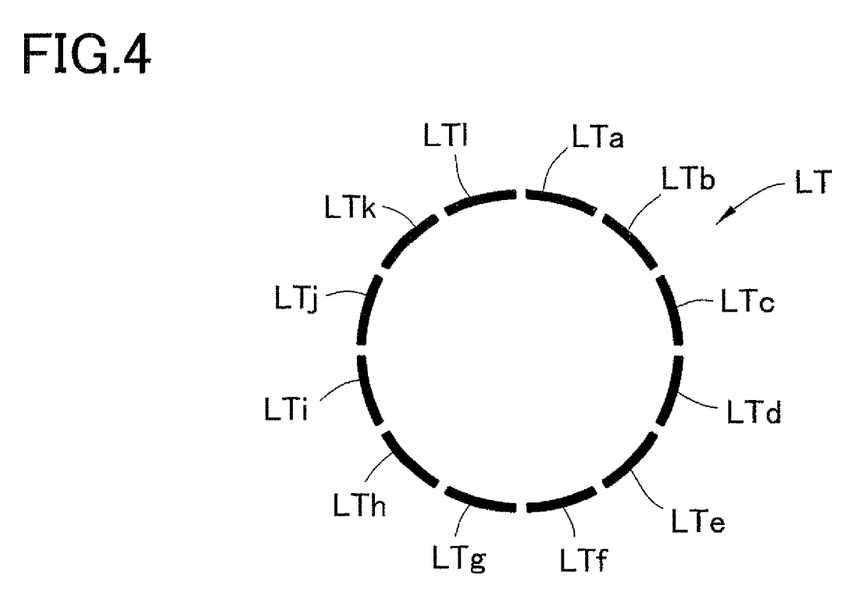
FIG. 4 is an explanatory view showing a display state of a reticule.
Figure 5A:
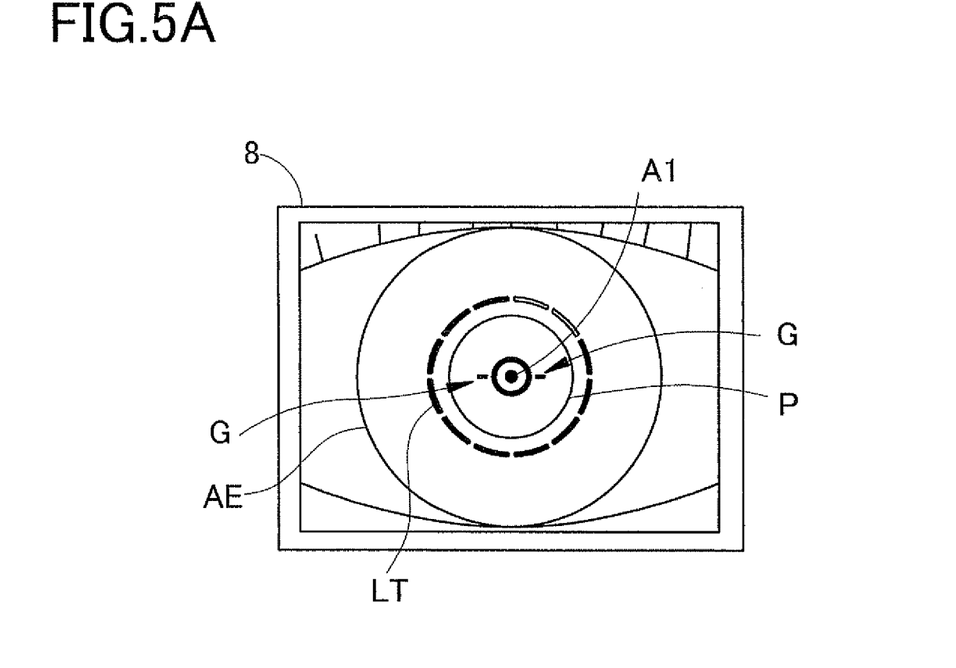
FIG. 5A is an explanatory view of an elapsed-time indication by use of an anterior-segment observation image.
Figure 5B:
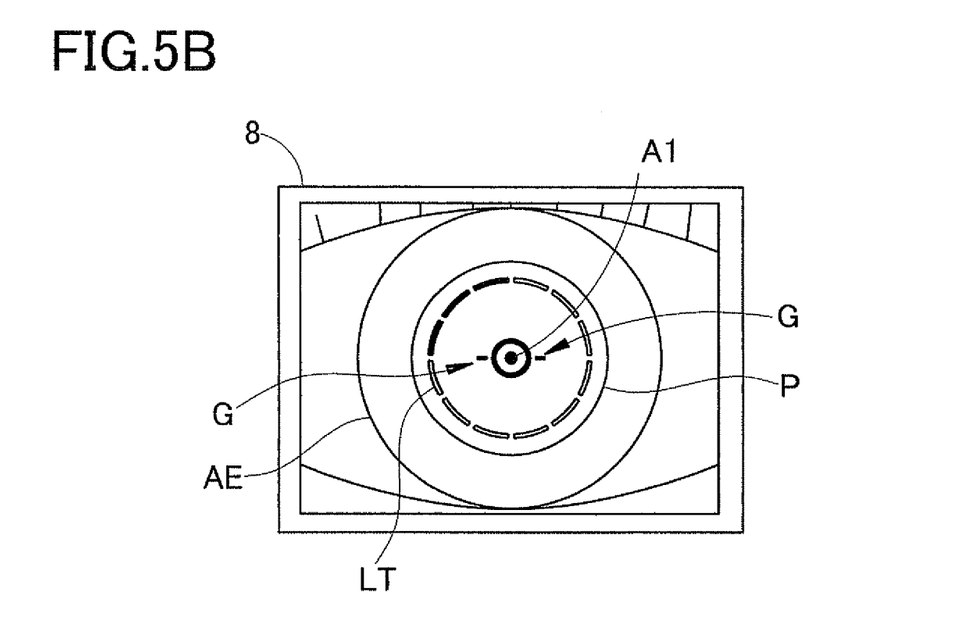
FIG. 5B is an explanatory view of the elapsed-time indication by use of the anterior-segment observation image.

FIG. 4 is an explanatory view (an enlarged view) showing changes in display state of the reticule LT. FIG. 5 show examples of the anterior-segment observation screen when the same examinee is to be re-photographed; FIG. 5A shows an example in which the anterior-segment AE constricted immediately after photographing of the fundus is displayed on the monitor 8 and FIG. 5B shows an example in which the anterior-segment AE naturally dilated to a certain degree after a lapse of a fixed time from photographing is displayed on the monitor 8. In FIG. 5, the index images Ma to Mh projected in a ring pattern are omitted to facilitate explanation of a relationship between the elapsed time measurement using the reticule LT and the pupil diameter P.

As shown in FIG. 4, the circular reticule LT in the present embodiment consists of a set of figures LTa to LTL designed by equally dividing the circular form into segments. In synchronization with counting of an elapsed time by the timer 86, the controller 80 can sequentially switch a display state of the figures LTa to LTL.

For instance, in accordance with the elapsed time from input of the trigger signal from the photographing switch 83, the controller 80 sequentially changes the display state of each of the figures LTa to LTL in the clockwise order from the figure LTa. This switching of the display state between the figures LTa to LTL is performed by changing the "color" or may be conducted by switching from highlight display to normal display in accordance with the elapsed time. Otherwise, the controller 80 has only to control display of the reticule LT to allow the examiner to ascertain the elapsed time based on switching of the display state between the figures LTa to LTL when the examiner looks at the reticule LT. Accordingly, the examiner can instinctively ascertain the elapsed time from the previous photographing.

In natural mydriasis of a normal examinee's eye, the above display of the elapsed time is provided in such a way that a waiting time determined in consideration of the time estimated to be required from constriction to a mydriatic state enabling next photographing is expressed as one cycle of the reticule, and this time is divided equally by the number of divided figures. For instance, when the time required for a general examinee's eye to dilate up to a pupil diameter needed for re-photographing is assumed to be 2 minutes, a time to be expressed in one cycle of the reticule LT consisting of twelve figures LTa to LTL is set to 3 minutes in consideration of the above required time. In this case, a time of 15 seconds is assigned to each figure. In other words, the controller 80 changes the display state of each figure every 15 seconds by counting the elapsed time with the timer 86. The time expressed by the reticule LT is not limited to 3 minutes and may be set in sufficient consideration of the waiting time estimated to be required from constriction to a mydriatic state enabling next photographing. Further, the number of dividing the reticule may also be set as required.

If the total time expressed by the figures LTa to LTL is assumed to 3 minutes, FIG. 5A shows a state after an elapsed time of as short as 30 seconds from previous photographing, so that the examiner easily ascertains that it is immediately after photographing. Subsequently, when the state comes to shown in FIG. 5B as the time passes, showing changes in display state of the figures LTa to LTi, it is found that about 2 minutes has passed. At that time, when the pupil diameter P is compared with the reticule LT, it is ascertained that the pupil diameter meets the desired pupil diameter and the examiner judges that the pupil is in a sufficient natural mydriatic state whereby enabling photographing. When it is judged from comparison with the reticule LT that sufficient mydriasis is obtained before a lapse of a predetermined time (e.g., 2 minutes) generally estimated to obtain sufficient mydriasis, a next photographing operation may be started. On the other hand, when it is judged from the comparison with the reticule LT that a sufficient mydriatic state is not obtained even after the predetermined time has passed, a waiting time for next photographing can be easily estimated by considering changes in display of remaining figures (elapsed time) and a mydriatic state at that time.

After the sufficient mydriatic state is ascertained, the photographing operation is started. The controller 80 causes the monitor 8 to change from the anterior-segment observation image to the fundus observation image based on a predetermined input signal and simultaneously terminates display of the reticule LT (terminates counting of the elapsed time by the timer 86). In this way, it is possible to efficiently display a time indicator in the form of the reticule to be used for determining photographing timing only during anterior-segment illumination needing to check the elapsed time. The controller 80 performs a similar fundus photographing operation to the above in response to a trigger signal from the photographing switch 83.

With the above configuration, it is possible for the examiner to compare the sizes between the reticule LT and the pupil diameter and simultaneously ascertain the elapsed time indicated by the figures LTa to LTl constituting the reticule LT. Accordingly, the examiner can easily grasp the mydriatic state corresponding to the elapsed time and adequately determines next photographing timing. Further, when the examiner checks the state of the pupil diameter while referring to the elapsed time indicated by the reticule LT, it is easy to judge whether the pupil is constricted or the pupil is naturally small. This enables the examiner to perform fundus photographing under more appropriate photographing conditions.

Figure 6:
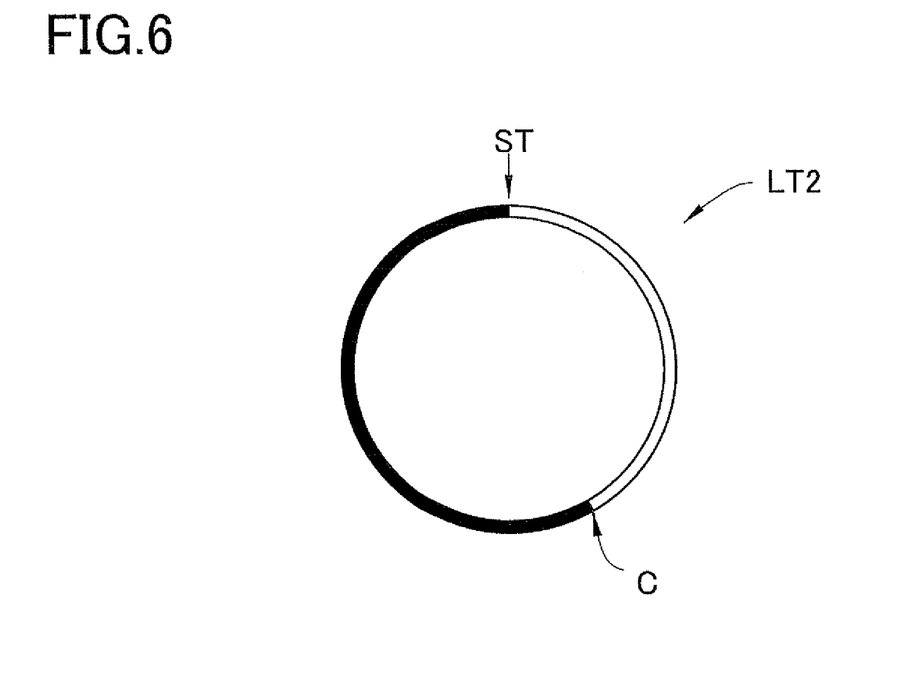
FIG. 6 is a modified example of the elapsed-time indication.

In the above example, the reticule LT consists of a plurality of figures and the elapsed time is expressed by the display state of each figure. As an alternative, FIG. 6 shows a modified example of an elapsed-time display in which an entire reticule LT2 is designed as a single smooth circle and display of the reticule LT2 may be switched linearly according to an elapsed time from previous photographing. For instance, changeover of a display state of the reticule LT2 is started from a start position ST, and a display changeover point C is shifted clockwise with time.

There is known that an elapsed time until the pupil constricted once becomes open tends to be slow with age. Thus, a waiting time and elapsed time information indicated by the reticule LT may be set according to age and others. For instance, as an examinee is older, the waiting time and the elapsed time indicated by the reticule LT are set to be longer. By this setting, a mydriatic state to the elapsed time can be ascertained properly with consideration given to examinee's age. For instance, information on a waiting time and information on an elapsed time indicated by the reticule LT are stored in advance in the memory 85 in association with each age group of examinees. In photographing, the examiner inputs the information such as examinee's age by operation of the input switch 84. The controller 80 thus controls display of the reticule LT with the waiting time and elapsed time corresponding to the input examinee's age.

As an alternative, an elapsed time using the reticule LT may be set according to a state of an eye, e.g., a disease state. For instance, an elapsed time of the reticule LT may be arbitrarily set according to the state of an eye by operation of the input switch 84.

Further, during the elapsed time indicated by the reticule LT, it may be arranged to inform the examiner with another signal (e.g., sound) of that a predetermined time has passed from previous photographing. For example, when half of the display state of the reticule LT is changed (when half of a waiting time has passed), a speaker not shown may be driven to make a sound to inform the examiner thereof. Even when the examiner turns his/her eyes away from the monitor 8, therefore, this sound makes it easier for the examiner to notice that a predetermined time has passed after photographing.

As an alternative, it may be arranged to arbitrarily set the timing to check the mydriatic state during the elapsed time indicated by the reticule LT by operation of the switch 84 and others. Accordingly, it is possible to unify the timing to determine natural mydriasis by examiner or facility.

In the above example, the examiner checks the pupil diameter and the reticule LT and then starts a manual photographing operation. As an alternative, an automatic fundus photographing operation may be started when an outer shape of the pupil diameter P detected by image processing in the controller 80 and the display position of the reticule LT are compared and the pupil diameter P is determined to have such a size that does not partially overlap the reticule LT. In this case, in consideration of the elapsed time of the timer 86 indicated by the reticule LT, it is preferable to perform comparison between the reticule LT and the pupil diameter P after at least a predetermined time elapsed after previous photographing (it is preferable to enable the start of photographing operation after the predetermined elapsed time). Accordingly, the examiner is allowed to more simply perform the fundus photographing.

The above example shows photographing of both eyes of one examinee. As well as such a case, the fundus photographing apparatus may be used to several times perform photographing of both a center portion and a peripheral portion of a fundus of one eye by changing a presenting position of a fixation target, thereby developing a panorama image of the fundus. In the peripheral photographing, a light beam enters the pupil from an oblique direction, and thus the photographing is more apt to be influenced by miosis.

In this case, therefore, the comparison in size between the reticule LT and the pupil diameter and the checking of the elapsed time indicated by the reticule LT are also simultaneously performed. This enables photographing at appropriate timings with reduced photographing errors.

Figure 7:
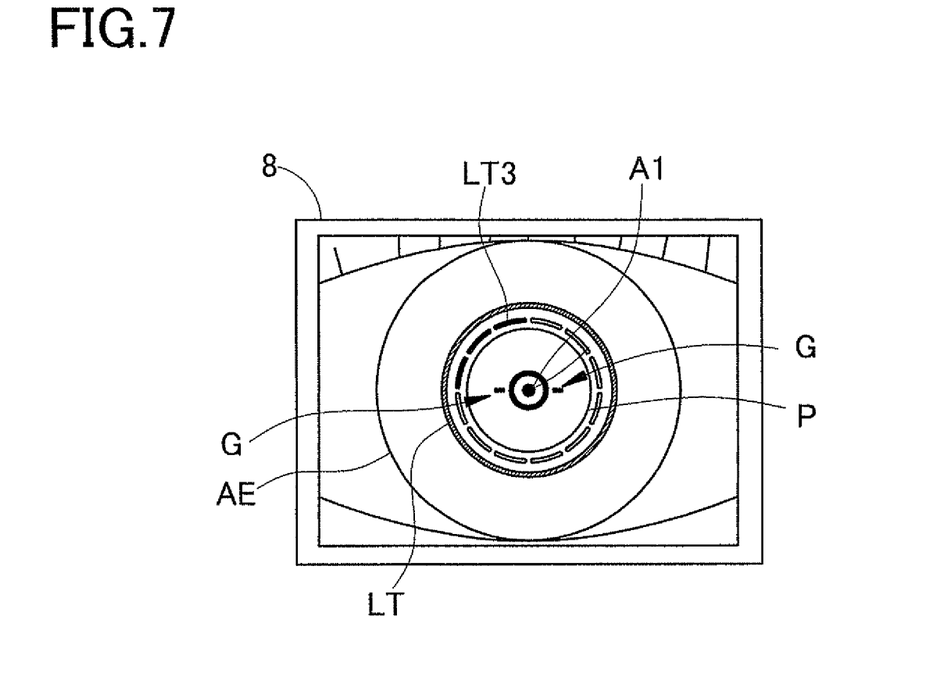
FIG. 7 is another modified example of the elapsed-time indication.

Furthermore, the above example shows the elapsed time from a photographing time by using the reticule LT indicating the desired pupil diameter. An alternative is to display an electronic graphic representing the elapsed time near the reticule LT as shown in FIG. 7. In this example, a reticule LT3 indicating a minimum pupil diameter enabling photographing of an examinee's eye is displayed near the inside of the reticule LT to indicate the elapsed time. As well as this example, a graphic display representing the elapsed time may be formed in a position to allow the examiner to check the display without moving his/her visual lines from the pupil displayed on the monitor 8.

The above example shows that, when the screen of the monitor 8 is changed to the fundus observation screen, display (and counting) of the elapsed time by the reticule LT is terminated. An alternative is to continue the display (counting) of the elapsed time even when the fundus observation image is displayed on the monitor 8. In this case, however, the elapsed time is displayed in numerals or the like in a position that does not interfere with the fundus image on the monitor 8. Alternatively, a thumbnail image of the anterior-segment observation image may be displayed together with the fundus image to continue a display of the elapsed time with the reticule LT on the thumbnail image.

While the presently preferred embodiment of the present invention has been shown and described, it is to be understood that this disclosure is for the purpose of illustration and that various changes and modifications may be made without departing from the scope of the invention as set forth in the appended claims.

The invention claimed is:

1. A fundus photographing apparatus for photographing a fundus of an examinee's eye, the apparatus comprising:
    a fundus photographing optical system including a visible light source and being arranged to image a fundus illuminated with visible light emitted from the visible light source and receive reflection light of the visible light reflected from the fundus to obtain a visible fundus image;
    a display controller arranged to cause a monitor to display an image of an anterior segment of the examinee's eye obtained by an observation image obtaining part;
    a photographing controller arranged to turn on the visible light source based on a photographing start signal from a photographing switch or a photographing start signal generated automatically, and to store in a memory the visible fundus image obtained by the fundus photographing optical system; and
    a time informing part arranged to inform an elapsed time beginning at input of the photographing start signal to cause the photographing controller to turn on the visible light source and store the visible fundus image, the elapsed time being a waiting time to next operation of the photographing controller to turn on the visible light source and store the visible fundus image, or an elapsed time beginning at turn-on of the visible light source by the photographing controller, the elapsed time being a waiting time to next operation of the photographing controller to turn on the visible light source and store the visible fundus image,
    the elapsed time being an elapsed time needed for a pupil constricted by the visible light to dilate naturally, and
    the display controller causing the monitor to simultaneously display the elapsed time and the anterior segment image of the examinee's eye.

2. The fundus photographing apparatus according to claim 1,
    wherein the observation part includes an anterior-segment observation optical system arranged to image the anterior segment illuminated with infrared light to obtain the anterior-segment image.

3. The fundus photographing apparatus according to claim 2, wherein the display controller displays a reticule indicating a desired pupil diameter needed for photographing on the monitor and simultaneously displays the elapsed time by changing a display state of the reticule with time.

4. The fundus photographing apparatus according to claim 3, further including an elapsed-time setting part arranged to set the elapsed time indicated by a change in the display state of the reticule,
    wherein the display controller changes the display state of the reticule with time on the monitor based on the elapsed time set by the elapsed-time setting part.

5. The fundus photographing apparatus according to claim 4, wherein the display controller displays the elapsed time by changing a color of the reticule.

6. The fundus photographing apparatus according to claim 1, wherein the display controller displays information on a waiting time required from first photographing to second photographing and information on the elapsed time obtained by the time informing part on the same screen of the monitor.

* * * * *